Figure 1:
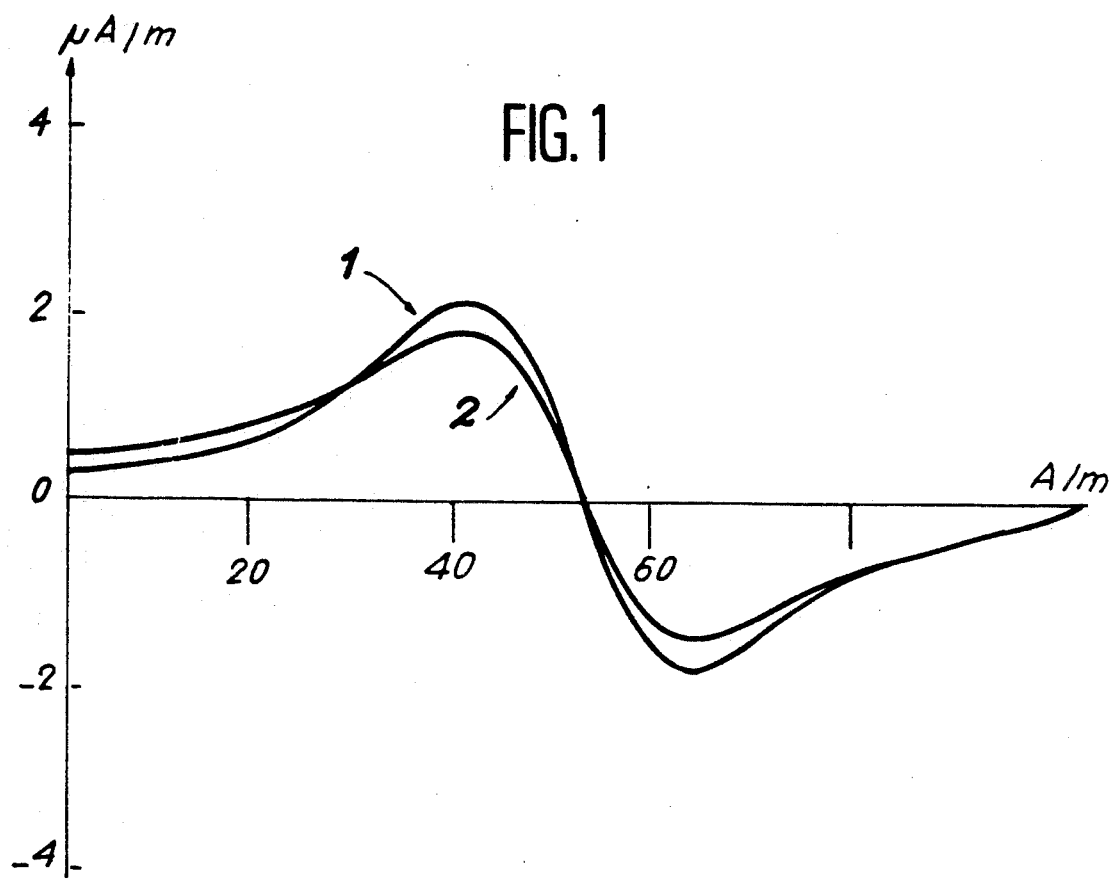

United States Patent [19]

Moussavi

[11] Patent Number: 5,254,478
[45] Date of Patent: Oct. 19, 1993

[54] USE IN MAGNETOMETRY BY ELECTRONIC PARAMAGNETIC RESONANCE (EPR) OF TETRACYANOQUINODIMETHANE DERIVATIVES

[75] Inventor: Mehdi Moussavi, Saint Egreve, France

[73] Assignee: Commissariat a l'Energie Atomique, France

[21] Appl. No.: 671,548

[22] Filed: Mar. 19, 1991

[30] Foreign Application Priority Data

Apr. 4, 1990 [FR] France ................... 90 04322

[51] Int. Cl.$^5$ ............................................. G01N 24/10
[52] U.S. Cl. ................................... 436/173; 324/300; 546/79; 546/108
[58] Field of Search .................. 436/173; 324/300; 546/79, 108

[56] References Cited

U.S. PATENT DOCUMENTS

| | | | |
|---|---|---|---|
| 3,162,641 | 12/1964 | Acker et al. | 546/347 X |
| 3,507,876 | 4/1970 | McConnell et al. | 436/173 X |
| 4,386,054 | 5/1983 | Takeuchi et al. | 436/173 X |
| 4,696,905 | 9/1987 | Aoyama et al. | 436/173 X |
| 4,996,311 | 2/1991 | Moussavi et al. | 540/139 |

OTHER PUBLICATIONS

J. D. Roberts et al. "Basic Principles of Organic Chemistry" 2nd ed., 1977, W. A. Benjamin, Inc., Menlo Park Calif., pp. 984-985, 1117-1118, and 1192-1193.

M. Windholz et al., Ed. "The Merck Index" 10th ed., 1983, Merck & Co., Inc., Rahway, NJ. entries 119, 1108, 7077, and 7991.

L. R. Melby et al. *J. Am. Chem. Soc.*, 1962, 84., 3374-3387.

S. Flandrois et al. *J. Chim. Phys. Physicochim. Biol.*, 1972, 69, 1305-1314.

Uemura et al. "Magnetic Properties and Spin Dynamics of an Organic Magnetic Salt 1-Methyl-3'-Ethyl-2,-2'-Quinaselenacyanine-[TCNQ]," *J. Phys. Soc. Jpn.*, 1982, 51, 760-766.

Acker et al. "7,7,8,8-Tetracyanoquinodimethane and its Electrically Conducting Anion-Radical Derivatives", *J. Am. Chem. Soc.*, 1960, 82, 6408-6409.

Banks, J. E. "Naming Organic Compounds" 2nd Ed., 1976, W. B. Saunders Company, Philadelphia, 257.

Chemical Abstracts Tenth Collective Index Chemical Substances 1981 pp. 7976CS, 7977CS, 9393CS, 9396CS, 9397CS, 9399CS, 37673CS, 37718CS, 38330CS, 46453CS.

Chemical Abstracts 55:23062e (Chesnut et al.).
Chemical Abstracts 56:5553f (Chesnut et al.).
Chemical Abstracts 60:1208f (Siemons et al.).
Chemical Abstracts 60:1208g (Kepler).
Chemical Abstracts 77:157985n (Flandvois et al.).

Compte Rendu des Seances Hebdomaclairs de L'Academie des Sciences, vol. 265, serie C, Oct. 2, 1967, pp. 688-690, Paris, FR; P. DuPuis et al.: "Conducitivite electrique de quelques complexes du tetracyanoquinodimethane".

Molecular Crystals and Liquid Crystals, vol. 32, 1976, pp. 209-213, Londres, GB; Delhaes et al.: "Etude comparative de la chaleur specifique et du paramagnetisme de sels de TCNQ a cations diamamagnetiques et reactions".

Tetrahedron Letters, no. 38, 1977, pp. 3325-3328, Oxford, GB: G. Saito et al.: "Synthesis of anion-radical salts by hydride transfer reactions".

*Primary Examiner*—James C. Housel
*Assistant Examiner*—Arlen Soderquist
*Attorney, Agent, or Firm*—Pearne, Gordon, McCoy & Granger

[57] ABSTRACT

Use in magnetometry by electronic paramagnetic resonance (EPR) of tetracyanoquinodimethane derivatives in accordance with the formula:

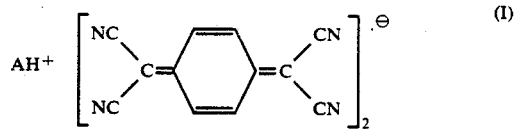

in which AH+ is a cation derived from a heterocyclic aromatic base having at least three aromatic rings and a single NH+ group included in at least one of the rings, AH+ being e.g. acridinium or benzoquinolinium.

5 Claims, 1 Drawing Sheet

USE IN MAGNETOMETRY BY ELECTRONIC PARAMAGNETIC RESONANCE (EPR) OF TETRACYANOQUINODIMETHANE DERIVATIVES

The present invention relates to the use of tetracyanoquinodimethane (TCNQ) derivatives in magnetometry by electronic paramagnetic resonance (EPR).

More specifically, it relates to the use in EPR magnetometry of organic charge transfer compounds of the type $(A_a)^+ (TCNQ_b)$·in which $a=1$, $b=2$ and A represents a cation derived from a heterocyclic aromatic base.

Charge transfer complexes of this type have been known since the early 1960's and have been studied for their electricity conducting properties. Examples of such complexes are e.g. described in Nature, vol. 309, 1984, pp. 119-126; Accounts of Chemical Research, vol. 12, No. 3, 1979, pp. 79 to 86; and FR-A-2 564 092.

Generally these organic complexes are used for their conducting or semiconducting properties. However, the use in EPR magnetometry of tetracyanoquinodimethane quinolinium has been envisaged and is described in FR-A- 2 603 384.

For use in EPR magnetometry, the most appropriate substances are those having a high magnetic susceptibility (1 to $4.10^{-4}$ in uem/ mole), a single low field signal (no hyperfine coupling) and a good stability of the solid state of the substance in the temperature use range of $-40°$ to $+70°$ C.

These qualities are represented by the merit factor of the material, which can be evaluated with the aid of the process and the apparatus described in FR-A- 2 634 556.

Moreover, it is interesting for these uses in EPR to find the paramagnetic substance whose production is easiest and least expensive and which will require less power for maintaining resonance in the magnetometer.

The volume serit factor of the tetracyanoquinodimethane quinolinium derivative, determined by using the process and apparatus of FR-A- 2 634 556 at a frequency of 1.845 MHz is $2.7.10^{-6}$. This value is obtained for the maximum high frequency power which can be supplied by the spectrometer, but in view of the high electrical conductivity of this substance, the high hf power necessary for obtaining a good signal makes the problem of direct coupling between the detection coil and the hf coil critical. Thus, the signal is distorted and it becomes difficult to regulate the magnetometer.

Moreover, the production of this paramagnetic substance requires complex purification and recrystallization operations, which lead to high preparation costs and times.

In addition, research has been carried out to find other paramagnetic substances having a merit factor at least equivalent thereto and equal or lower line widths, but which require lower hf power levels for maintaining the paramagnetic resonance.

The present invention specifically relates to the use in EPR of TCNQ derivatives having improved properties and which-comply with the formula:

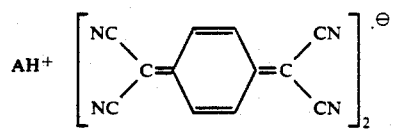
(I)

in which AH+ is a cation derived from a heterocyclic aromatic base having three aromatic nuclei and a single NH+ group included in one of these nuclei.

It is pointed out that, according to the invention, the term "aromatic nucleus" covers a benzene nucleus or a benzene-analogous heterocyclic nucleus, i.e. having $\pi$ electrons, as is e.g. the case with the pyridine nucleus.

According to the invention, the cation derived from said heterocyclic aromatic base has a single NH+ group and the latter can be included in one of the aromatic nuclei.

For example, the AH+ cation can be chosen from among benzoquinolinium, acridinium, phenothridinium, phenothiazinium, phenarsazinium and benzoisoauinolinium cations, which can optionally be substituted by alkyl radicals having 1 to 8 carbon atoms.

These possible substitutions can only exist on the carbon atoms of the aromatic nuclei, because for use in EPR magnetometry, it is important that the nitrogen atom of the cation is linked with a hydrogen atom. Thus, the N-alkyl derivatives of quinoline or acridine have an excessive conductivity for said application.

As examples of tetracyanoquinodimethane derivatives according to the invention, reference can be made to:

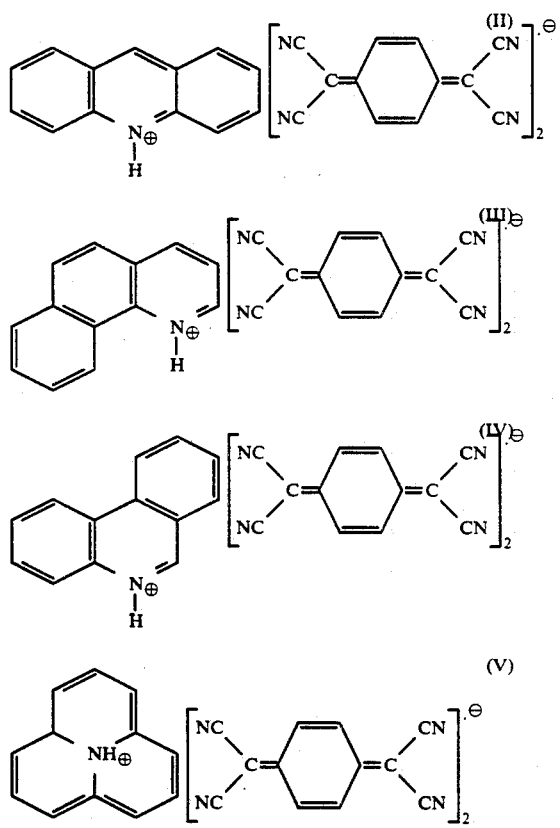

In the derivative according to the invention, the fact of replacing the quinolinium cation by a cation having at least three aromatic nuclei makes it possible to obtain a greater compactness, have a greater extension of the $\pi$ electron cloud, whilst retaining the planar structure of the molecule and this leads to a better spin dynamic and less wide resonance lines, which consequently require less hf power for maintaining the resonance.

The invention also relates to a process for the preparation of tetracyanoquinodimethane derivatives in accordance with formula (I). This process consists of reacting an iodide of AH+ with tetracyanoquinodimethane.

This reaction can be carried out in an organic solvent such as acetonitrile by adding the iodide solution of AH+ to a TCNQ solution in an organic solvent at boiling point.

The starting product, i.e. the iodide of AH+ can be prepared by reacting the aromatic base A corresponding to the cation AH+ with hydroiodic acid. This reaction can be carried out in a solvent such as ethanol.

The invention also relates to an electronic paramagnetic resonance magnetometer using as the substance having an electronic magnetic moment the tetracyanoquinodimethane derivative according to the invention.

Advantageously, said magnetometer comprises an enclosure containing a substance having an electronic magnetic moment, a first winding wound around said enclosure and able to produce a voltage due to a magnetic flux variation resulting from the precession of the electronic magnetic moment of said substance about an ambient magnetic field (HO), said voltage having a so-called Larmor frequency equal to $\gamma HO/2\pi$, in which $\gamma$ is the gyromagnetic ratio of the substance used, a second winding able to produce a rotary magnetic field (Hl) at said Larmor frequency for maintaining the precession and electronic means able, on the one hand, to measure the frequency of the signal taken at the terminals of the first winding, which gives the modulus of the ambient magnetic field (HO) and, on the other hand, to deliver the maintenance field (Hl), and uses as the substance having an electronic magnetic moment the tetracyanoquinodimethane derivative according to the invention.

Other characteristics and advantages of the invention will become apparent from reading the following examples given in an illustrative and non-limitative manner and with reference to the attached drawings, wherein show:

FIG. 1 the dispersion curves of the TCNQ derivatives.

Figure 2:
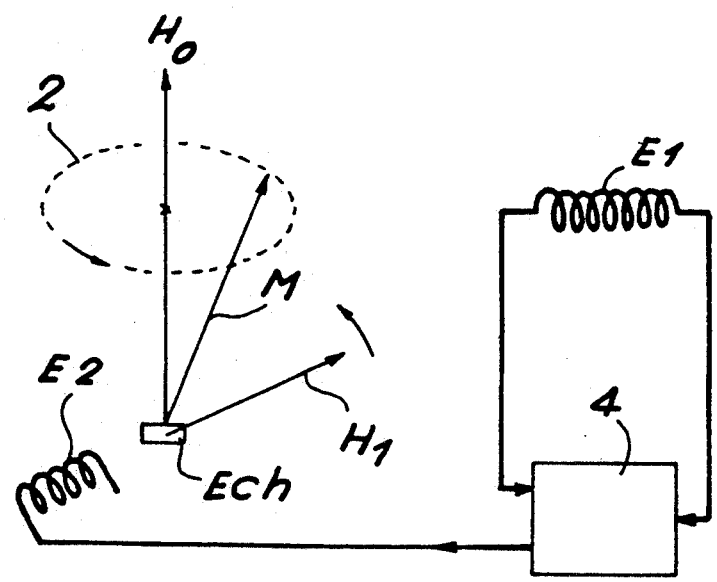

FIG. 2 diagrammatically an EPR magnetometer.

EXAMPLE 1: PREPARATION OF ACRIDINIUM BIS TETRACYANOQUINODIMETHANE OF FORMULA

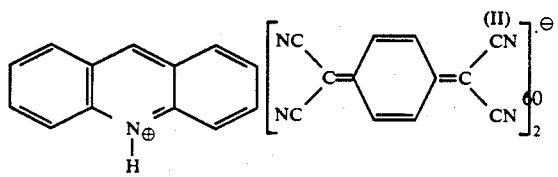

a) Preparation of Acridinium iodide

This reaction corresponds to the following reaction diagram:

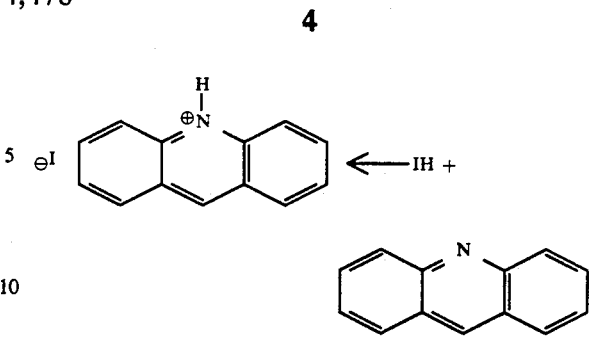

Dropwise addition takes place of 1.5 g (7.5 mmole) of 65% hydroiodic acid to a 1.35 g (7.5 mmole) solution of acridine in 20 ml of ethanol. Towards the end of the addition an orange precipitate appears. Ethanol is then added accompanied by heating to 50 to 60° C. until the said precipitate has completely dissolved (approximately 20 ml of ethanol). Cooling takes place in the refrigerator and the acridinium iodide is filtered. In this way 2.2 g of a redorange monocrystalline solid are recovered corresponding to a 96% yield.

b) Preparation of acridinium bis tetracyanoquinodimethane

This is followed by the reaction of the acridinium iodide obtained in stage a) with TCNQ in accordance with the following reaction diagram:

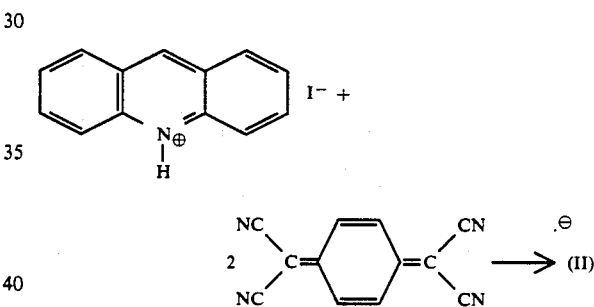

A solution of 0.8 g of acridinium iodide in 25 ml of acetonitrile is added to a solution of 1 g (5 mmole) of pure TCNQ in 250 ml of boiling acetonitrile, whilst operating under reflux and an argon atmosphere. After refluxing for 30 min., cooling of the reaction mixture takes place under argon and after standing for 2 h the precipitate is filtered and in this way 1 g of acridinium bis tetracyanoquinodimethane is recovered, which is washed with ether and gives a 34% yield.

EXAMPLE 2: PREPARATION OF BENZOQUINOLINIUM BIS TETRACYANOQUINDODIMETHANE OF FORMULA

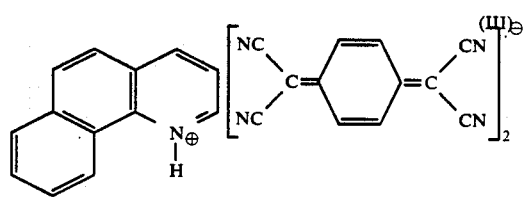

The same operating procedure as in Example 1 is adopted for preparing the TCNQ derivative, except that in stage a) use is made for the preparation of the iodide of 7.5 mmole of benzoquinoline instead of 7.5 mmole of acridine. This gives the benzoquinolinium bis tetracyanoquinodimethane with a 30% yield.

EXAMPLE 3

In this example determination takes place of the properties of the TCNQ derivatives prepared in Examples 1 and 2 for EPR magnetometry. To this end, determination takes place of the merit factor, the line width, the hf power necessary for maintaining the resonance and the lf modulation using the spectrometer described in FR-A-2 634 556. The results obtained are given in the following table.

TABLE

| TCNQ Derivative | Merit factor | Line width (A/m) | hf power (A/m) | lf modulation (A/m) |
|---|---|---|---|---|
| Quinolinium bis TCNQ | $2.7.10^{-6}$ | 20.2 | 22.5 | 9.5 |
| Acridinium bis TCNQ (ex 1) | $2.9.10^{-6}$ | 18.7 | 11.2 | 10 |
| Benzoquinolinium bis TCNQ (ex 1) | $2.0.10^{-6}$ | 18 | 9 | 10 |

This table gives as a comparative example the results obtained with quinolinium bis tetracyanoquinodimethane obtained from quinolinium iodide following the same process as in the invention.

On the basis of these results, it is apparent that the merit factor increases on changing from quinoline to acridine, but that it is lower with henzoquinoline. Conversely the line width decreases on changing from quinoline to acridine and to benzoquinoline. The same applies with respect to the hf pressure, which significantly decreases, whereas the lf modulation is equivalent for the three derivatives.

Thus, the derivatives according to the invention are of greater interest than quinolinium bis TCNQ. Moreover, they are less expensive to prepare because benzoquinolinium and acridinium iodides can be prepared more easily, in a few minutes, even in large quantities and require no special purification, which is not the case with quinolinium iodide.

FIG. 1 diagrammatically shows the dispersion curve of the acridinium bis TCNQ derivative according to the invention (curve 1) and the dispersion curve of the quinolinium bis TCNQ derivative (curve 2) plotted with the spectrometer described in FR-A-2 634 556 at a frequency of 1.846 MHz. FIG. 1 shows that the derivative according to the invention gives better results.

FIG. 2 diagrammatically shows an EPR magnetometer using the derivatives according to the invention and more particularly intended for the measurement of weak magnetic fields, which can have application in geophysics, mining prospecting, military and space detection and industrial robotics.

The existence of the spin of the electron and consequently a nonzero magnetic moment is the cause of the precession movement of the electron around the axis of the ambient magnetic field. The precession or Larmor frequency is determined by the following relation:

$$F = \gamma HO/2\pi$$

in which HO is the modulus of the ambient field and $\gamma$ the gyromagnetic ratio of the electron.

The principle of an electronic paramagnetic resonance magnetometer consists of detecting the variation of the magnetic flux produced by the precession of the magnetic moment of a paramagnetic substance. For this purpose use is made of a winding sensitive to the variable induction, which leads to the appearance at the terminals of said winding of an a.c. voltage, which is at the Larmor frequency. The measurement of this frequency gives the value of the field.

FIG. 2 illustrates this principle. The precession movement of the macroscopic magnetization M of a paramagnetic substance sample Ech around the axis of the ambient field HO is symbolized by the circle 2. This magnetization is the sum of the elementary contributions of the magnetic moments of the electron of the substance. At the terminals of a winding El appears a voltage, whose amplitude is proportional to the square of the modulus of the field HO and whose frequency is equal to the Larmor frequency. A measuring circuit makes it possible to measure these two quantities.

In order to maintain the precession movement of the macroscopic magnetization, it is necessary to pull the latter by a rotary field Hl at the Larmor frequency. This field must have a component perpendicular to HO. For this purpose use is made of a second winding E2, which is supplied by the circuit 4 with a voltage at a frequency as close as possible to the Larmor frequency.

The magnetometer is consequently an apparatus which measures the frequency of the voltage induced by the precession of the magnetization and which also produces a pulling field, whose frequency must be permanently linked with the modulus of the ambient field.

According to the invention, the paramagnetic substance sample used in this magnetometer is constituted by a tetracyanoquinodimethane derivative of formula (i).

I claim:

1. A magnetometric method of measuring a magnetic field by electromagnetic paramagnetic resonance using applied high frequency power and a tetracyanoquinodimethane derivative as a paramagnetic substance having an electronic magnetic moment the improvement comprising selecting as the paramagnetic substance a tetracyanoquinodimethane derivative of the formula:

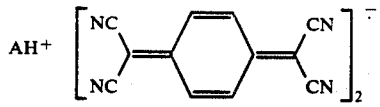

in which $AH^{30}$ is a cation derived from a heterocyclic aromatic base having three aromatic rings and a single heteroatom included in one of the rings as an $NH^+$ group, exposing said paramagnetic substance to a magnetic field to be measured, and measuring the magnetic field by detecting the variation of the magnetic flux produced by the precession of the magnetic moment of said paramagnetic substance, whereby a reduced level of applied high frequency power is required compared to measuring a magnetic field using electromagnetic paramagnetic resonance without using said cation.

2. A method according to claim 1, wherein $AH^{30}$ is selected from the group consisting of benzoquinolinium, acridinium, phenanthridinium, and benzoisoquinolinium cations.

3. A method according to claim 1, wherein $AH^+$ represents:

4. A method according to claim 1, wherein AH+ represents:
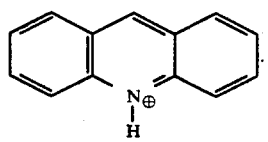
5. A method according to claim 1, wherein AH+ represents:
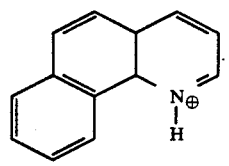
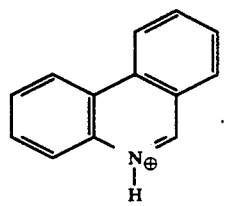
* * * * *